US012680073B2

(12) United States Patent
Kumar et al.

(10) Patent No.: US 12,680,073 B2
(45) Date of Patent: Jul. 14, 2026

(54) BIOPROCESS FOR THE SIMULTANEOUS PRODUCTION OF POLYHYDROXYBUTYRATE AND VIOLACEIN PIGMENT FROM HIMALAYAN BACTERIUM IODOBACTER SP. PCH 194

(71) Applicant: COUNCIL OF SCIENTIFIC AND INDUSTRIAL RESEARCH AN INDIAN REGISTERED BODY INCORPORATED UNDER THE REGN. OF SOC. ACT (ACT XXI OF 1860), New Delhi (IN)

(72) Inventors: Vijay Kumar, Palampur Himachal Pradesh (IN); Sanjay Kumar, Palampur Himachal Pradesh (IN); Dharam Singh, Palampur Himachal Pradesh (IN)

(73) Assignee: COUNCIL OF SCIENTIFIC AND INDUSTRIAL RESEARCH AN INDIAN REGISTERED BODY INCORPORATED UNDER THE REGN. OF SOC. ACT (ACT XXI OF 1860), New Delhi (IN)

( * ) Notice: Subject to any disclaimer, the term of this patent is extended or adjusted under 35 U.S.C. 154(b) by 587 days.

(21) Appl. No.: 18/044,328

(22) PCT Filed: Sep. 7, 2021

(86) PCT No.: PCT/IN2021/050868
    § 371 (c)(1),
    (2) Date: Mar. 7, 2023

(87) PCT Pub. No.: WO2022/054081
    PCT Pub. Date: Mar. 17, 2022

(65) Prior Publication Data
    US 2023/0332098 A1     Oct. 19, 2023

(30) Foreign Application Priority Data

Sep. 12, 2020    (IN) .............................. 202011039834

(51) Int. Cl.
    *C12N 1/205*        (2026.01)
    *C12P 7/625*        (2022.01)
    *C12P 17/18*        (2006.01)
    *C12R 1/01*         (2006.01)
(52) U.S. Cl.
    CPC .............. *C12N 1/205* (2021.05); *C12P 7/625* (2013.01); *C12P 17/182* (2013.01); *C12R 2001/01* (2021.05)
(58) Field of Classification Search
    CPC . C12N 1/205; C12N 1/20; C12P 7/625; C12P 17/182; C12P 17/16; C12R 2001/01
    See application file for complete search history.

(56) References Cited

U.S. PATENT DOCUMENTS

| 7,129,068 B2 | 10/2006 | Bordoloi et al. |
| 7,666,636 B2 | 2/2010 | Yezza et al. |
| 2016/0338360 A1 | 11/2016 | Mitter et al. |

FOREIGN PATENT DOCUMENTS

| EP | 2545181 B1 | 11/2014 |
| WO | WO-2015100431 A2 | 7/2015 |
| WO | WO-2022054081 A1 | 3/2022 |

OTHER PUBLICATIONS

Atalah J, Blamey L, Munoz-Ibacache S, Gutierrez F, Urzua M, Encinas MV, Paez M, Sun J, Blamey JM. Isolation and characterization of violacein from an Antarctic Iodobacter: a non-pathogenic psychrotolerant microorganism. Extremophiles. Jan. 2020;24(1):43-52. (Year: 2020).*
Kumar P, Jun HB, Kim BS. Co-production of polyhydroxyalkanoates and carotenoids through bioconversion of glycerol by Paracoccus sp. strain LL1. International Journal of Biological Macromolecules. Feb. 1, 2018;107:2552-8. (Year: 2018).*
Kumar V, Thakur V, Ambika, Kumar S, Singh D. Bioplastic reservoir of diverse bacterial communities revealed along altitude gradient of Pangi-Chamba trans-Himalayan region. FEMS microbiology letters. Jul. 2018;365(14):fny144. (Year: 2018).*
Rambo CR, Costa CM, Carminatti CA, Recouvreux DO, d'Acampora AJ, Porto LM. Osteointegration of poly-(3-hydroxybutyrate-co-3-hydroxyvalerate) scaffolds incorporated with violacein. Materials Science and Engineering: C. Mar. 1, 2012;32(2):385-9. (Year: 2012).*
"Japanese Application Serial No. 2023516222 Notice of Reasons for Rejection mailed Apr. 22, 2024", with English translation, 6 pages.

(Continued)

*Primary Examiner* — Jennifer M.H. Tichy
*Assistant Examiner* — Emily F Eix
(74) *Attorney, Agent, or Firm* — Schwegman Lundberg & Woessner, P.A.

(57) ABSTRACT

The present disclosure provides a bioprocess for the simultaneous production of Polyhydroxybutyrate (PHB) and Violacein pigment in a single fermentation using a Himalayan bacterial isolate *Iodobacter* sp. PCH 194, having accession number MTCC 25171. PHB has plastic properties, renewable origin and bio-degradable nature. It can be used for various packaging applications replacing the petrochemicals-based plastics, thus providing greener alternative to environment. Violacein pigment has anti-oxidant, anti-tumoral, anti-bacterial, and photo-protective properties and can be used in cosmetics and pharmaceuticals applications. The present disclosure provides production process of two valuable products i.e. PHB and violacein pigment in a single bioprocess, therefore, is economically attractive, time saving, and commercially feasible process.

6 Claims, 7 Drawing Sheets

(56) References Cited

OTHER PUBLICATIONS

Atalah, Joaquin, "Isolation and characterization of violacein from an Antarctic Iodobacter: a non-pathogenic psychrotolerant microorganism", Extremophiles, 2020, vol. 24, (Jan. 2020), 10 pages.

Logan, Niall A., "Numerical Taxonomy of Violet Pigmented Gram Negative Bacteria and Description of Iodobacter fluviatile gen nov comb nov", International Journal of Systematic Bacteriology 39, (Oct. 1989), 7 pages.

Bornscheuer, Uwe T., et al., "Feeding on plastic A bacterium completely degrades poly(ethylene terephthalate)", Science, vol. 351, Issue 6278, (Mar. 11, 2016), 1154-1156.

"International Application No. PCT/IN2021/050868, International Search Report and Written Opinion mailed Dec. 15, 2021", (Dec. 15, 2021), 8 pgs.

Duran, Nelson, et al., "Advances in Chromobacterium violaceum and properties of violacein-Its main secondary metabolite: A review", Biotechnol. Adv. 34:1030-1045, (2016), 16 pgs.

Fang, Ming-Yue, et al., "High crude violacein production from glucose by Escherichia coli engineered with interactive control of tryptophan pathway and violacein biosynthetic pathway", Fang et al. Microbial Cell Factories (2015) 14:8; DOI 10.1186/s12934-015-0192-x, (Jan. 16, 2015), 13 pgs.

Kumar, Vijay, et al., "Bioplastic reservoir of diverse bacterial communities revealed along altitude gradient of Pangi-Chamba trans-Himalayan region", FEMS Microbiology Letters, vol. 365, Issue 14, Jul. 2018, fny144, https://doi.org/10.1093/femsle/fny144; Bornscheuer UT. 2016 Feeding on plastic, Science 351:1154-1155), (Jun. 14, 2018), 9 pgs.

Pena, C., et al., "Biotechnological strategies to improve production of microbial poly-(3-hydroxybutyrate): a review of recent research work", Microbial Biotechnology (2014) 7(4), 278-293; doi:10.1111/1751-7915.12129, (2014), 278-293.

Sathiyanarayanan, Ganesan, et al., "Production and characterization of medium-chain-length polyhydroxyalkanoate copolymer from Arctic psychrotrophic bacterium Pseudomonas sp. PAMC 28620", International Journal of Biological Macromolecules 97 (2017) 710-720, (Jan. 17, 2017), 710-720.

Wang, Ying, et al., "Polyhydroxyalkanoates, challenges and opportunities", Current Opinion in Biotechnology 2014, 30:59-65, (Jun. 26, 2014), 59-65.

* cited by examiner

BIOPROCESS FOR THE SIMULTANEOUS PRODUCTION OF POLYHYDROXYBUTYRATE AND VIOLACEIN PIGMENT FROM HIMALAYAN BACTERIUM IODOBACTER SP. PCH 194

PRIORITY CLAIM TO RELATED APPLICATIONS

This application is a U.S. national stage filing under 35 U.S.C. § 371 from International Application No. PCT/IN2021/050868, filed on 7 Sep. 2021, and published as WO2022/054081 on 17 Mar. 2022, which claims the benefit under 35 U.S.C. 119 to India application No. 202011039834, filed on 12 Sep. 2020, the benefit of priority of each of which is claimed herein, and which applications and publication are hereby incorporated herein by reference in their entirety.

FIELD OF THE INVENTION

The present invention relates to a bioprocess for the simultaneous production of Polyhydroxybutyrate (PHB) and Violacein pigment in a single fermentation using a novel bacterial isolate *Iodobacter* sp. PCH 194 (MTCC 25171). The present invention also relates to the dual products PHB and Violacein pigment that are produced in a specific medium under defined set of growth conditions, and further to a downstream process has been developed for the extraction and recovery of PHB and Violaccin pigment.

BACKGROUND OF THE INVENTION

Most of the biomolecules and biopolymers are derived from nature in order to meet several needs of the human kind. PHB is a linear polyester of 3-hydroxybutarate and has gained much attention because of its biodegradable and elastomeric properties. Majority of the polymers are derived from petrochemicals. The major concern with the use of petrochemical based polymers is their non-biodegradable nature besides causing environmental pollution and threat to fossil resources. Approximately 311 million ton/year plastics are produced globally and 90% of these are synthesized from petroleum (Bornscheuer UT. 2016 *Feeding on plastic. Science* 351:1154 1155) thereby leading to million tons of CO2 and other harmful emissions. In addition, non-degradable nature of plastic leads to the accumulation in million tons in the land and oceans, causing serious threat to food web and ecosystem. Therefore, there is an urgent need to explore an alternative and reliable source of polymers which can fulfill the need of society in an eco-friendly manner.

Many bacteria are reported to produce PHB and several biotechnological strategies have been employed to improve the PHB production, but commercial feasibility at an economic value still remains a concern. A number of research studies and inventions have come across in the past to produce PHB and to use low cost carbon source to reduce the production cost (U.S. Pat. No. 7,129,068B2. U.S. Pat. No. 7,666,636B2) but still they are not competing with petrochemical based plastic (Wang Y, et al. 2014 *Polyhydroxyalkanoates, challenges and opportunities. Curr. Opin. Biotechnol.* 30:59 65). Further, the PHB based bioplastics are comparatively costlier to the conventional petrochemical based plastics due to their higher production cost.

Violacein pigment contains violacein and deoxyviolacein which are violet-blue colored secondary metabolites, derivatized from indole and produced by several bacteria such as *Chromobacterium, Janthinobacterium* etc. Violacein have various important biological activities such as antioxidant, antitumoural, antibacterial, antiviral and antiprotozoa (Duran N, et al., 2016. *Advances in Chromobacterium violaceum and properties of violacein—Its main secondary metabolite: A review. Biotechnol. Adv.* 34:1030-1045). Violacein and deoxyviolacein are also used in various cosmetics and anti-sunscreen due to their antioxidant, antimicrobial and photo protective nature.

Furthermore, in the textile industries, violacein and deoxyviolacein are used as coloring agents. Violacein and deoxyviolacein are produced by various bacterial strains (Fang M, et al. 2015. *High crude violacein production from glucose by Escherichia coli engineered with interactive control of tryptophan pathway and violacein biosynthetic pathway. Microb. Cell Fact.* 14:8) and patents on process of their production and extraction have been made (EP 2545181B1).

It is thus clearly evident that, the prior arts have reported separate processes for the individual production of Polyhydroxybutyrate and Violacein pigment, but none of them offers a single bioprocess for the simultaneous production products i.e. Polyhydroxybutyrate and Violacein pigment which is commercially feasible.

Accordingly, keeping in view the drawbacks of the hitherto reported prior art, there exists a dire need to reduce the overall cost of production of Polyhydroxybutyrate as well as violacein pigment by providing an economical and commercially viable single bioprocess for the simultaneous production of both biomolecules namely PHB and Violacein pigment in a single fermentation reaction using glucose as sole carbon source.

OBJECTIVES OF THE INVENTION

The main objective of the present invention is therefore to provide a process for the simultaneous production of PHB and violacein pigment in single fermentation using a novel bacterial strain under defined set of physiological growth conditions and media which obviates the limitations of the hitherto reported prior art.

The second objective of the present invention is to provide an isolated pure bacterial strain of *Iodobacter* sp. PCH 194 (MTCC 25171).

The third objective of the invention is to use glucose as single carbon source and tryptone as nitrogen source for simultaneous production of PHB and Violacein pigment. The fourth objective of the invention is to provide a simple process for the separation, extraction and recovery of Violacein pigment and PHB from the culture broth.

SUMMARY OF THE INVENTION

In an aspect of the present disclosure, there is provided a bioprocess for the simultaneous production of polyhydroxybutyrate (PHB) and violet-blue violacein pigment using the isolated bacterial strain of *Iodobacter* sp. MTCC 25171, the process comprising the steps: (i) inoculating a loopful of *Iodobacter* sp. MTCC 25171 in 50 mL sterile nutrient broth medium and incubating at a temperature of 20±2° C. for 32 to 36 hours at 100 to 200 rpm to obtain a seed culture for inoculating the production medium; (ii) inoculating 3 to 5% (v/v) of the seed culture as obtained in step [i] to a sterile production medium and incubating for 90 to 100 hours at 100 to 200 rpm, at a temperature of 20±2° C. to obtain a biomass; (iii) harvesting the biomass as obtained in step [ii] to obtain a pigmented cell pellet by centrifugation or microfiltration; (iv) suspending the pigmented cell pellet as obtained in step [iii] in methanol or ethanol in a volume ratio of 1:3 to 1:5 and mixing well for 10 to 15 minutes at room temperature followed by centrifugation to obtain a pigment in the supernatant; and repeating the step until no visible violet colour remains in the cell pellet to obtain a colourless cell pellet; (v) concentrating the supernatant as obtained in step [iv] using vacuum evaporation to obtain the desired violacein pigment; (vi) suspending the colourless cell pellet as obtained in step [iv] in 3 to 5 times the volume of 1:1 trichloromethane and bleaching solution, followed by incubating overnight at temperature ranging from 30 to 40° C. under continuous shaking to obtain a mixture; (vii) allowing the mixture as obtained in step [vi] to stand for a time period of 10 to 15 minutes and pipetting out the lower organic layer in a test-tube and then adding 3 to 5 times the volume of chilled methanol, followed by mixing it well and keeping at temperature ranging from minus 4 to minus 20° C. for a time period of 30 to 60 minutes for precipitation to obtain a reaction mixture; (viii) centrifuging the reaction mixture as obtained in step [vii] to collect the pellet as precipitate and removing the residual solvent; (ix) drying the pellet as obtained in step [viii] and re-dissolving it in trichloromethane; and (x) repeating steps (vi to viii) and finally collecting the pellet of Polyhydroxybutyrate by allowing the residual solvent to evaporate.

In a second aspect of the present disclosure, there is provided a bioprocess for the simultaneous production of polyhydroxybutyrate (PHB) and violet-blue violacein pigment using the isolated bacterial strain of *Iodobacter* sp. MTCC 25171 as disclosed herein, wherein the PHB obtained is useful for the preparation of biodegradable bio plastics.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

DETAILED DESCRIPTION OF THE INVENTION

Figure 1:
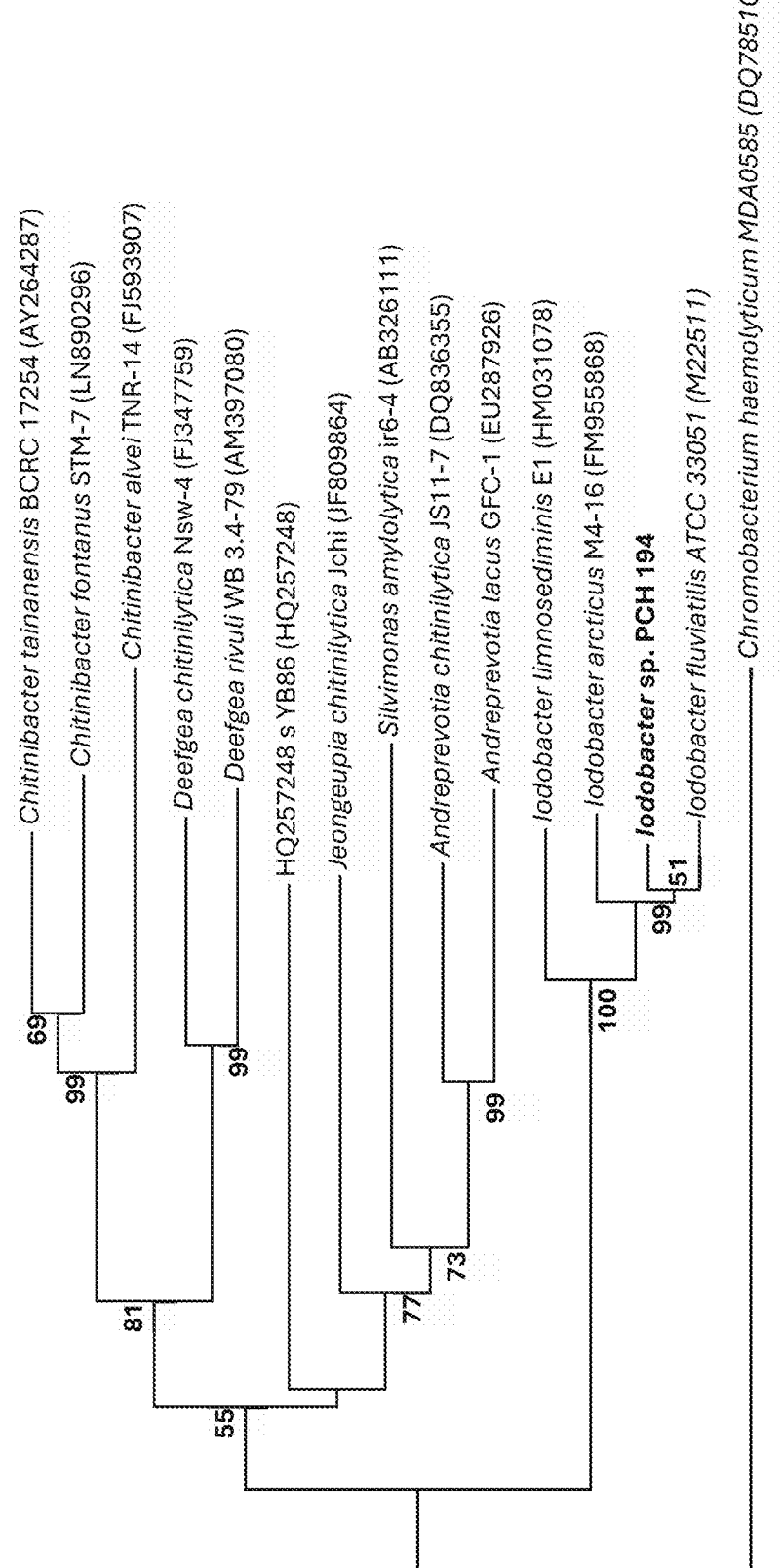
FIG. 1 depicts the neighbor-joining phylogenetic tree based on 16S rDNA sequences showing phylogenetic position of *Iodobacter* sp. PCH 194 with related bacteria and type strain (similarity mentioned at the end of entry). Tree constructed in MEGA6 with 1000 bootstrapping, scale bar represent 0.01 substitution per nucleotide and number in parenthesis are the GenBank accession number of the sequences.

The invention will now be described in detail in connection with certain preferred and optional embodiments, so that various aspects thereof may be more fully understood and appreciated.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a mixing speed in the range of 100 rpm to 200 rpm should be interpreted to include not only the explicitly recited limits of about 100 rpm to about 200 rpm but also to include sub-ranges, such as 120 rpm to 175 rpm, and so forth, as well as individual amounts, within the specified ranges, such as 150 rpm, and 186 rpm.

The term "20±2° C." refers to the temperature in the range of 18 to 22° C.

The present disclosure is not to be limited in scope by the specific embodiments described herein, which are intended for the purposes of exemplification only. Functionally-equivalent products, compositions, and methods are clearly within the scope of the disclosure, as described herein.

The present disclosure provides a bioprocess for the simultaneous production of two valuable products, i.e., polyhydroxybutyrate (PHB) and violacein pigment in a single bioprocess using the novel isolated bacterial strain of *Iodobacter* sp. PCH194 [MTCC 25171]. Apart from the scientific and economic benefits, the present disclosure is of high relevance to social and environmental aspect.

PHB has the utility for the production of biodegradable bioplastics. Therefore, PHB based bioplastics can fulfill the requirement of society in an eco-friendly manner. In addition, the bioplastics made of PHB can significantly contribute to reduction in pollution caused by plastic in a sustainable and long-term manner. The market for polyhydroxyalkanoates is projected to grow at a CAGR of 4.88% from USD 73.6 million in 2016 to USD 93.5 million by 2021.

Second product of the bioprocess of the present disclosure is violacein pigment, which is blue-violet colored secondary metabolite containing violacein and deoxyviolacein as major constituents. Violacein has various important biological activities such as anti-oxidant, anti-tumoral, anti-bacterial, and photo-protective properties. Therefore, violacein pigment has applications in textiles, pharmaceuticals and cosmetic industries.

The present disclosure further provides a pure bacterial strain of *Iodobacter* sp. PCH 194 [MTCC 25171], wherein the said *Iodobacter* sp. colonies are violet-colored, gram-negative, glucose fermenting and grow optimally at a temperature of 20° C.

In an embodiment of the present disclosure, there is provided a bioprocess for the simultaneous production of polyhydroxybutyrate (PHB) and violet-blue violacein pigment using the isolated bacterial strain of *Iodobacter* sp. MTCC 25171, the process comprising the steps:

i) inoculating a loopful of *Iodobacter* sp. MTCC 25171 in sterile nutrient broth medium and incubating at a temperature of 20±2° C. for 32 to 36 hours at 100 to 200 rpm to obtain the seed culture for inoculating the production medium;

ii) inoculating 3 to 5% (v/v) of the seed culture as obtained in step [i] to the sterile production medium and incubating for 90 to 100 hours at 100 to 200 rpm at a temperature of 20±2° C. to obtain a biomass;

iii) harvesting the biomass as obtained in step [ii] to obtain a pigmented cell pellet by centrifugation or microfiltration;

iv) suspending the pigmented cell pellet as obtained in step [iii] in methanol or ethanol in a volume ratio of 1:3 to 1:5 and mixing well for 10 to 15 minutes at room temperature followed by centrifugation to obtain a pigment in the supernatant; and repeating the step until no visible violet colour remains in the cell pellet to obtain a colourless cell pellet;

v) concentrating the supernatant as obtained in step [iv] using vacuum evaporation to obtain the desired violacein pigment;

vi) suspending the colourless cell pellet as obtained in step [iv] in 3 to 5 times the volume of 1:1 trichloromethane and bleaching solution, followed by incubating overnight at temperature ranging from 30 to 40° C. under continuous shaking to obtain a mixture;

vii) allowing the mixture as obtained in step [vi] to stand for 10 to 15 minutes and pipetting out the lower organic layer in a test-tube and then adding 3 to 5 times the volume of chilled methanol, followed by mixing it well and keeping at temperature ranging from minus 4 to minus 20° C. for 30 to 60 minutes for precipitation to obtain a reaction mixture;

viii) centrifuging the reaction mixture as obtained in step [vii] to collect the pellet as precipitate and removing the residual solvent;

ix) drying the pellet as obtained in step [viii] and re-dissolving it in trichloromethane; and x) repeating steps (vi to viii) and finally collecting the pellet of Polyhydroxybutyrate by allowing the residual solvent to evaporate.

In an embodiment of the present disclosure, there is provided a bioprocess for the simultaneous production of polyhydroxybutyrate (PHB) and violet-blue violacein pigment using the isolated bacterial strain of *Iodobacter* sp. MTCC 25171 as disclosed herein, the production medium of the process comprises of glucose 4% (w/v), tryptone 0.5% (w/v), NaCl 0.1% (w/v) and 25 mM $K_2HPO_4/KH_2PO_4$, pH 7.5, and inoculated with 4% (v/v) seed.

In an embodiment of the present disclosure, there is provided a bioprocess for the simultaneous production of polyhydroxybutyrate (PHB) and violet-blue violacein pigment using the isolated bacterial strain of *Iodobacter* sp. MTCC 25171 as disclosed herein, wherein the time period for the production of PHB and violacein pigment ranges from 36 to 100 hours at a temperature of 20° C. with continuous shaking at 150 rpm. In another embodiment of the present disclosure, the time period for the process of production ranges from 36 to 98 hours, with continuous shaking at 150 rpm. In yet another embodiment of the present disclosure, the time period for the process of production is 96 hours, with continuous shaking at 150 rpm.

In an embodiment of the present disclosure, there is provided a bioprocess for the simultaneous production of polyhydroxybutyrate (PHB) and violet-blue violacein pigment using the isolated bacterial strain of *Iodobacter* sp. MTCC 25171 as disclosed herein, wherein the process results in the production of coloured biomass in the range of 7 to 9 g/L dry cell weight after harvesting using centrifugation from 1 liter of culture broth.

In an embodiment of the present disclosure, there is provided a bioprocess for the simultaneous production of polyhydroxybutyrate (PHB) and violet-blue violacein pigment using the isolated bacterial strain of *Iodobacter* sp. MTCC 25171 as disclosed herein, wherein the process results in the production of coloured biomass in range of 13 to 19 g/L dry cell weight after centrifugation or microfiltration of 7.5 or 10 liter fermenter broth using Akta Flux microfiltration system (GE Healthcare). 7.5 culture broth was concentrated with 0.2 μm hollow fiber cartridge and residual violet pigmented cell slurry than collected and centrifuged. After centrifugation, both supernatant and pallets were collected for further extraction of violacein pigment and PHB. Viscous supernatant treated with 3 to 5 times of volume of methanol or ethanol and stirred using magnetic stirrer. This mixture was again passed in Akta flux system or centrifuged to obtain Violacein pigment as filtrate or supernatant. In another embodiment of the present disclosure, there is provided a bioprocess for the simultaneous production of polyhydroxybutyrate (PHB) and violet-blue violacein pigment using the isolated bacterial strain of *Iodobacter* sp. MTCC 25171 as disclosed herein, wherein the cell pellet of the process is treated with methanol, mixed well at room temperature and centrifuged, and repeating the step until the pellet becomes colorless. In yet another embodiment of the present disclosure, the supernatant was simultaneously collected in each step by evaporating in a rotary vacuum evaporator.

In another embodiment of the present disclosure, there is provided a bioprocess for the simultaneous production of polyhydroxybutyrate (PHB) and violet-blue violacein pigment using the isolated bacterial strain of *Iodobacter* sp. MTCC 25171 as disclosed herein, wherein the solvents used for the extraction may be selected from the group consisting of methanol, ethanol, or butanol, in a ratio ranging from 1:3 to 1:5 and repeating the extraction step for 2 to 3 times until no further colour remains in the cell pellet. In yet another embodiment of the present disclosure, the crude extract of Violacein pigment was concentrated by vacuum evaporator.

In another embodiment of the present disclosure, there is provided a bioprocess for the simultaneous production of polyhydroxybutyrate (PHB) and violet-blue violacein pigment using the isolated bacterial strain of *Iodobacter* sp. MTCC 25171 as disclosed herein, wherein the colourless cell pellet is treated with 3 to 5 times the volume of 1:1 trichloromethane and bleaching solution under continuous shaking condition at 37° C. for overnight.

In another embodiment of the present disclosure, there is provided a bioprocess for the simultaneous production of polyhydroxybutyrate (PHB) and violet-blue violacein pigment using the isolated bacterial strain of *Iodobacter* sp. MTCC 25171 as disclosed herein, wherein the mixture of cell pellet, trichloromethane and bleaching solution which is incubated overnight is allowed to stand still for 10 to 15 minutes and the lower organic layer is pipetted out in a test-tube or container and 1:5 to 1:10 volume of chilled methanol was added thereto and mixed well and kept at a temperature in the range of minus 4° C. to minus 20° C. for 30 to 60 minutes and centrifuged.

In another embodiment of the present disclosure, there is provided a bioprocess for the simultaneous production of polyhydroxybutyrate (PHB) and violet-blue violacein pigment using the isolated bacterial strain of *Iodobacter* sp. MTCC 25171 as disclosed herein, wherein the pellet was collected, dried and re-dissolved in trichloromethane and the methanol precipitation step was repeated and finally the pellet of PHB was collected and dried to evaporate the residual solvents.

In an embodiment of the present disclosure, there is provided a bioprocess for the simultaneous production of polyhydroxybutyrate (PHB) and violet-blue violacein pigment using the isolated bacterial strain of *Iodobacter* sp. MTCC 25171 as disclosed herein, wherein the time period for the production of PHB and violacein pigment in fermenter ranges from 36 to 100 hours while maintaining 20% dissolved oxygen and 150 rpm. In another embodiment of the present disclosure, the time period for the production of PHB and violacein pigment in fermenter is 96 hours. In an embodiment of the present disclosure, there is provided a bioprocess for the simultaneous production of polyhydroxybutyrate (PHB) and violet-blue violacein pigment using the isolated bacterial strain of *Iodobacter* sp. MTCC 25171 as disclosed herein, wherein the yield of PHB and Violaccin pigment obtained from 1 liter culture broth is in the range of 3 to 5 g/L (>50% of dry cell biomass), and 0.5 to 0.8 g/L, respectively.

In an embodiment of the present disclosure, there is provided a bioprocess for the simultaneous production of polyhydroxybutyrate (PHB) and violet-blue violaccin pigment using the isolated bacterial strain of *Iodobacter* sp. MTCC 25171 as disclosed herein, wherein the yield of PHB and Violacein pigment from 7.5 or 10 liter fermenter broth is in the range of 7 to 10 g/L (>50% of dry cell biomass), and 0.8 to 1.5 g/L, respectively.

In another embodiment of the present disclosure, there is provided a bioprocess for the simultaneous production of polyhydroxybutyrate (PHB) and violet-blue violaccin pigment using the isolated bacterial strain of *Iodobacter* sp. MTCC 25171 as disclosed herein, wherein the PHB and Violaccin pigment production is not limited only on 4% (w/v) glucose and 0.5% (w/v) tryptone, but can be produced by using various concentrations thereof.

In yet another embodiment of the present disclosure, the PHB and Violacein pigment production is not limited only on glucose and tryptone, but can be achieved on various organic carbon and various inorganic and organic nitrogen sources.

In another embodiment of the present disclosure, there is provided a bioprocess for the simultaneous production of polyhydroxybutyrate (PHB) and violet-blue violacein pigment using the isolated bacterial strain of *Iodobacter* sp. MTCC 25171 as disclosed herein, wherein the PHB and Violacein pigment production is not limited to the temperature of 20° C. pH 7.5, 20% dissolved oxygen and 150 rpm but can be achieved in wider pH, temperature, oxygen and rpm conditions.

In an embodiment of the present disclosure, there is provided a bioprocess for the simultaneous production of polyhydroxybutyrate (PHB) and violet-blue violacein pigment using the isolated bacterial strain of *Iodobacter* sp. MTCC 25171 as disclosed herein, wherein the yield of PHB (PHB/carbon source) ranges from 0.18 to 0.25 g/g.

In another embodiment of the present disclosure, the volumetric productivity of PHB is in range of 0.075 to 0.104 g/L/h.

In another embodiment of the present disclosure, the fermentation is performed in a variable pH range in context to the initial pH 7.5 during fermentation.

In another embodiment of the present disclosure, there is provided a bioprocess for the simultaneous production of polyhydroxybutyrate (PHB) and violet-blue violaccin pigment using the isolated bacterial strain of *Iodobacter* sp. MTCC 25171 as disclosed herein, wherein the PHB obtained has melting temperature (Tm) of 178+5° C. and crystallization temperature of 50±5° C.

In an embodiment of the present disclosure, there is provided a bioprocess for the simultaneous production of polyhydroxybutyrate (PHB) and violet-blue violacein pigment using the isolated bacterial strain of *Iodobacter* sp. MTCC 25171 as disclosed herein, wherein the PHB obtained is useful for the preparation of biodegradable bio plastics. In an embodiment of the present disclosure, there is provided a bioprocess for the simultaneous production of polyhydroxybutyrate (PHB) and violet-blue violacein pigment using the isolated bacterial strain of *Iodobacter* sp. MTCC 25171 as disclosed herein, wherein the violacein pigment obtained exhibits antimicrobial, anti-cancerous and photo protective properties.

EXAMPLES

Following examples are given by way of illustration and therefore should not be construed to limit the scope of the invention.

Details of Biological Resources Used in the Invention

The bacterial strain *Iodobacter* sp. PCH194 was isolated from the mud sediment sample of glacial lake in high altitude of Pangi and Chamba region in the western Himalayas, Himachal Pradesh, 176316, India. The bacterial isolate PCH194 was identified on the basis of partial 16S rDNA sequencing and phylogenetic analysis with reference strains. The bacterial strain, *Iodobacter* sp. PCH 194 was deposited at MTCC, CSIR-IMTECH, Chandigarh, India with accession no. MTCC 25171 on Jul. 13, 2018.

Methodology

Isolation and identification of bacterial strain

Sediment samples were collected from a glacial lake at high altitude of Pangi-Chamba region in the western Himalayas and transported to laboratory at 4° C. Sediment sample was plated directly in duplicate on Antarctic Bacterial agar medium (ABM). The plates were incubated at 20° C. until colonies appeared and pure bacterial colonies were further streaked in nutrient agar medium (NA). The violet color colony was purified by streaking on NA plates and identified by 16S rDNA sequencing using DNA ABI 3130XL Genetic Analyzer (Applied Biosystems). The bacterial isolate PCH194 is violet-colored (most intensely in the centers of spreading colonies), gram negative, small rod, cells are straight round-ended rods, facultative anaerobes, oxidase and catalase positive, glucose fermenting and can grow at 4 to 28° C. with optimum growth at 20° C. Molecular characterization of partial 16S rDNA sequence has shown >99% sequence similarity with *Iodobacter fluviatilis* ATCC 33051 (T) and phylogenetic analysis also showed closest match with this type strain (FIG. 1). The bacterial culture can be maintained in nutrient agar plate at 4° C. with sub-culturing after 20 to 30 days or in glycerol stock at −80° C. with sub-culturing after every 6 months.

Production of PHB and Violacein Pigment in 1 Liter Flask, 7.5 and 10 Liter Working Volume of Fermenter The production of PHB and violacein pigment were carried out in 1 liter working volume in a flask using the optimized production medium components (Glucose 4%, tryptone 0.5%, NaCl 0.1% and phosphate buffer components 25 mM) pH 7.5 and production conditions (90-100 hours incubation at 20° C. and 150 rpm). For further scale up, a 7.5 and 10 liter working volume of a 23.5 liter fermenter was run using the slightly higher medium components (in % (w/v) of glucose 4.25%, tryptone 0.55%, NaCl 0.1% and potassium phosphate buffering components at 25 mM concentration) and medium pH was set to 7.5. The fermenter was inoculated with 4% (w/v) of seed (32 to 36 hours old) and incubated for 90-100 hours at 20° C. at 150 rpm, keeping the pH uncontrolled and $pO_2$ was set auto at 20%. The antifoaming agent (Antifoam SE-15, Sigma) of 1.0 or 2.0 ml to the fermenter was added as per requirement to limit the froth formation in a fermenter.

Downstream Processing of Violacein Pigment from Biomass

The biomass of the culture broth was harvested after 96 hours by centrifugation (10,000 g for 10 minutes, at 4 to 10° C.) from 1 liter culture broth and from 7.5 or 10 liter fermenter broth by microfiltration using Akta Flux system (GE Healthcare, USA). Harvested pigmented cell pellet was suspended with methanol or ethanol in a ratio of 1:3 to 1:5 and mixed well for few minutes at room temperature and then centrifuged to obtain the pigment in supernatant. This step was repeated until no visible violet color remained in the cell pellet.

The culture broth from 7.5 or 10 liter fermenter was concentrated using microfiltration in Akta flux system. The retentate was mixed with 3 to 5 times the volume of methanol and stirred using magnetic stirrer. This mixture was again passed in Akta flux system and the violacein pigment was collected as filtrate. The retentate was again treated with methanol and the process was repeated until cell pellet becomes colorless. The extracted violacein pigment solution was concentrated and dried using a rotary vacuum evaporator to obtain the desired bacterial crude violacein pigment.

Downstream Processing of PHB from Biomass

The remaining colorless cell pellet was suspended in 3 to 5 times the volume of 1:1 trichloromethane and bleaching solution and was incubated overnight at 37° C. under continuous shaking conditions. The mixture was allowed to stand and cooled for a few minutes and lower organic layer was pipetted in a separate tube or reagent bottle. To this, chilled methanol was added (1:5 to 1:10 volume), mixed well and kept at temperature ranging from minus 4 to minus 20° C. for 30 to 60 minutes and centrifuged. PHB pellets were again dissolved in trichloromethane and precipitation step repeated again. Finally, PHB pellets were collected and dried to evaporate residual solvents and quantified.

Quantification and Chemical Profiling of Polyhydroxyalkanoates and Violacein Pigment Absorbance of violacein pigment was measured at 570 nm and spectral analysis (300 to 700 nm) was carried out in multiplate reader (BioTek Instruments, USA). The crude methanol extract was dried in vacuum rotavapour, weighed and re-dissolved in HPLC grade methanol for further analysis. A standard curve of violacein pigment was prepared by dissolving known amount in methanol and recording the absorbance at 570 nm. This curve was used for the estimation of violacein pigment in further assays. Chemical profiling, quantification and characterization of violacein pigment were carried out in UPLC-MS.

Determination of Monomer Composition of Polyhydroxyalkanoates Using GC-MS

Monomeric composition of PHA was determined by GCMS analysis in GCMS-QP2010 (Shimadzu) of methanolysed samples. Digestion and derivatization of purified PHA was carried out by using method as described (Sathiyanarayanan G, et al., 2017. *Production and characterization of medium-chain-length polyhydroxyalkanoates copolymer from Arctic psychrotrophic bacterium Pseudomonas sp. PAMC 28620. Int. J. Biol. Macromol.* 97:710-720; Kumar V, et al., 2018. *Bioplastic reservoir of diverse bacterial communities revealed along altitude gradient of Pangi-Chamba trans-Himalayan region. FEMS Microbiol. Lett.* 365: fny144). NIST/EPA/NIH library was searched to identify the monomer of PHA by comparing the corresponding mass ion of each peak.

Characterization

NMR Analysis

For NMR analysis, the purified PHA was dissolved in deuterated chloroform (CDCl3) for the determination of chemical structure by using proton ($^1$H) and carbon ($^{13}$C) NMR. NMR spectra were recorded using a Bruker Avance III 600 (Bruker Co., Fallanden, Switzerland). The $^1$H and $^{13}$C spectra were obtained at 500 and 150 MHz, respectively at room temperature. Chemical shifts such as resonance signals (δ) were given in ppm comparative to the outstanding signals of CDCl3 as an internal reference ($^1$H NMR: 7.26 ppm; $^{13}$C NMR: 77.42).

Preparation of Bioplastic Film of PHB and Analysis of its Physical Properties

Thin film of PHB was prepared by dissolving purified PHB in trichloromethane and evaporating the solvent. The thermal properties such as melting temperature (Tm) and crystallization temperature (Tc) was calculated using the out sourcing facilities provided by Nation Physical Laboratory, New Delhi.

Isolation, Identification and Phylogeny of PCH194

The bacterium is violet-colored, gram negative, facultative anaerobes, sugar fermenting and can grow at 4 to 30° C. with optimum growth at 20° C.

The bacterial culture can be maintained in nutrient agar plate at 4° C. with sub-culturing after every 15 to 20 days or in glycerol stock at –80° C. with sub-culturing after every 6 months.

Molecular characterization of partial 16S rDNA sequence has shown >99% sequence similarity with *Iodobacter fluviatilis* ATCC 33051 (T) and phylogenetic analysis also showed closest match with this type strain (FIG. 1). *Iodobacter* sp. PCH194 is a psychrophile and has shown the PHB and violacein pigment production potential.

Growth Profile

*Iodobacter* sp. PCH194 have shown good biomass production at 20° C. This bacterium has the ability to synthesize PHB and violacein pigment.

Effect of various carbon sources on growth and PHA production revealed that the glucose is preferred source of energy and led to highest biomass as well as accumulation of PHB (>50%). Fructose and maltose are also turn out to be good for growth and PHB production, but comparatively less utilized as compared to glucose. Glycerol, lactose, sucrose, tri-sodium citrate and potassium sodium tartrate are not utilized efficiently by the bacterium and resulted in lower biomass and PHB production.

Among various nitrogen sources tryptone turned out be very good nitrogen source for both PHB and violacein pigment synthesis. Other nitrogen sources such as peptone, yeast extract may also be used but resulted in lower PHB yield. Among inorganic nitrogen sources $NH_4Cl$ and $NH_4SO_4$ showed good biomass as well as production of both PHB and violacein pigment but comparatively lesser. (no clarity in the statement)

Figure 2:
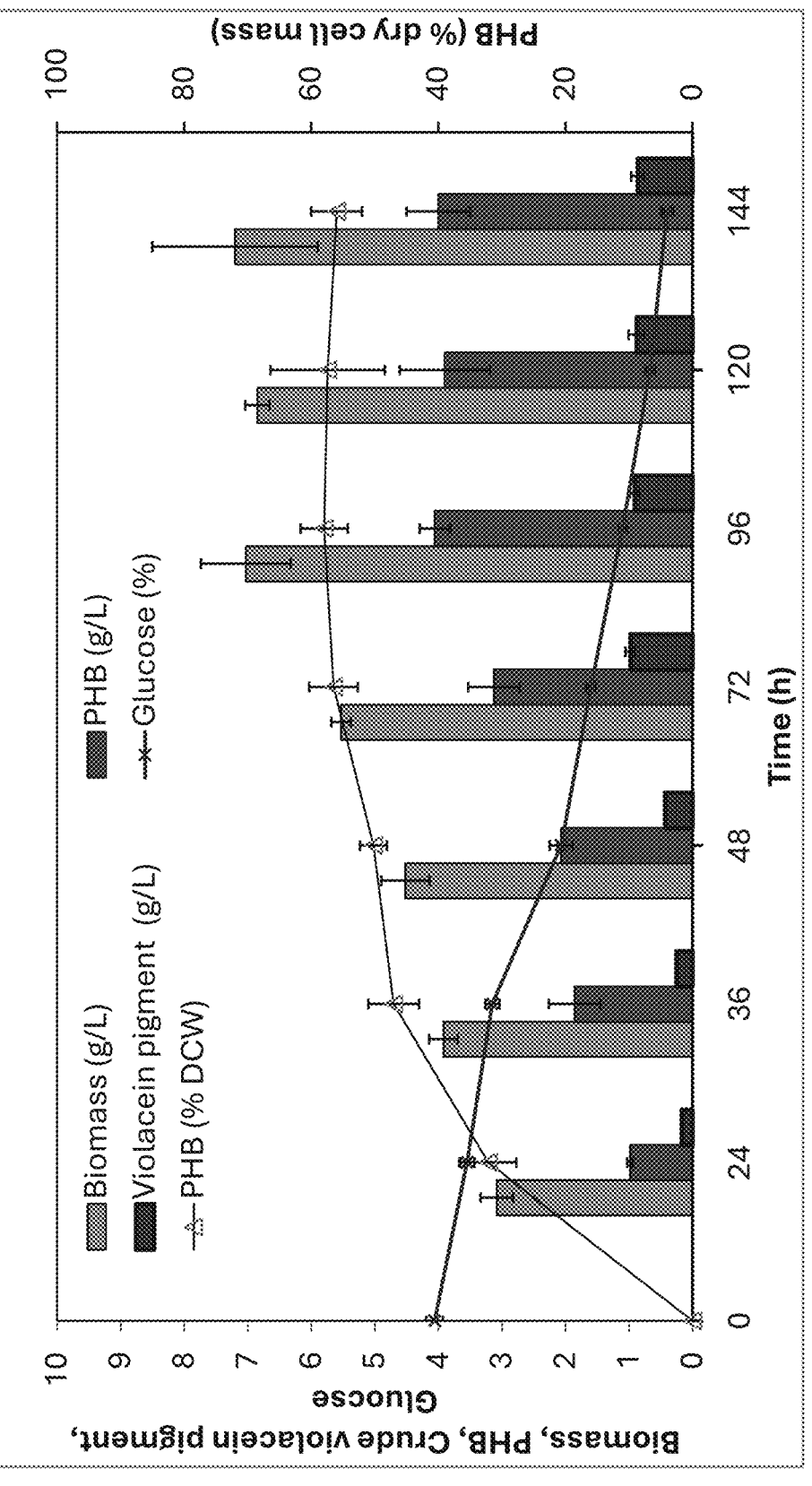
FIG. 2 depicts the biomass, glucose utilization, PHB and Violacein pigment production profile of *Iodobacter* sp. PCH 194 in 1 liter production medium, pH 7.5 at 20° C. and 150 rpm.

A typical growth curve and fermentation profile shown in FIG. 2 revealed that the production of PHB and violet pigment started after 24 hours and increased steadily along with the cell mass and attained highest production in stationary phase.

Production and extraction of PHB and violacein pigment in 1 liter flask conditions The production of PHB and violacein was carried out in 1 liter scale in shake flask resulted in the production of 7 to 9 g/L of dry cell biomass in 90-100 hours of incubation and cell density remain almost constant up to 144 hours. The cells harvested after 96 hours of incubation were used for the extraction of PHB and Violacein pigment as discussed. The yield of PHB and crude Violacein pigment from 1 liter culture of said process after 96 hours is in range of 3 to 5 g/L (>50 of dry cell biomass) and 0.5 to 0.8 g/L, respectively (FIG. 2).

Figure 3:
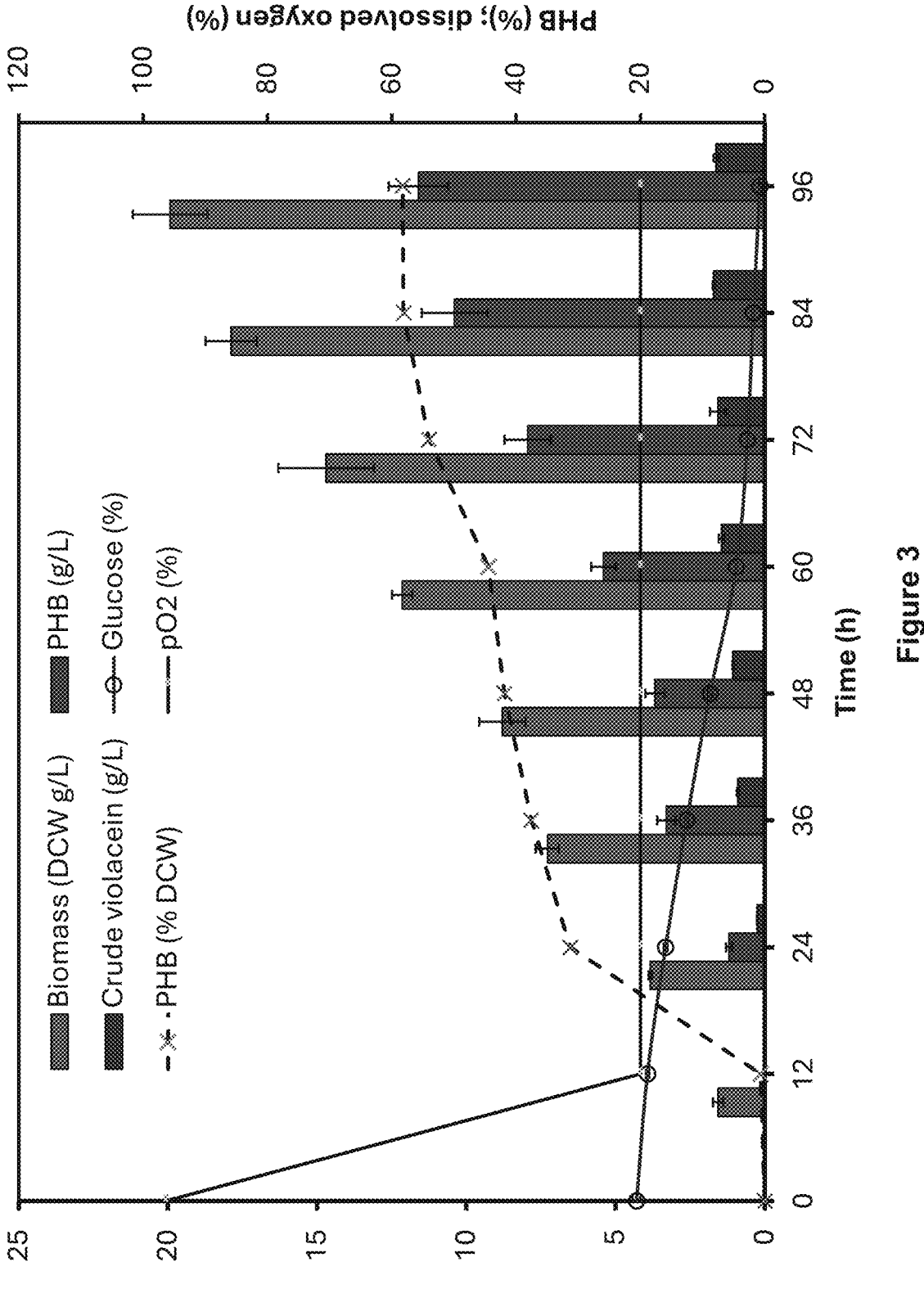
FIG. 3 depicts the simultaneous production of PHB and violacein pigment in 7.5 liter working volume of fermenter by *Iodobacter* sp. PCH194.

Production and Extraction of PHB and Violacein Pigment in 7.5 or 10 Liter Fermenter In a 7.5 or 10 liter working volume of fermenter using a constant DO (20%), the cell $OD_{600}$ reached to ≥15 in 90-100 hours of fermentation and dry cell weight was 16 to 19 g/L. After the harvesting the biomass and the extraction process as discussed, the yield of PHB and violacein pigment of said process was found to be in range of 7 to 10 g/L (>50% of dry cell biomass) and 0.8 to 1.5 g/L, respectively (FIG. 3). The presence of $O_2$ is necessary for the production of Violacein, however, the bacterium can produce PHB in facultative anaerobic condition. Therefore, $pO_2$ level was maintained at 20% for the simultaneous production of PHB and violacein pigment using *Iodobacter* sp. PCH 194 bacterium in the said process.

Analysis of PHB, PHB Based Bioplastic Film and Violacein Pigment

Figure 4:
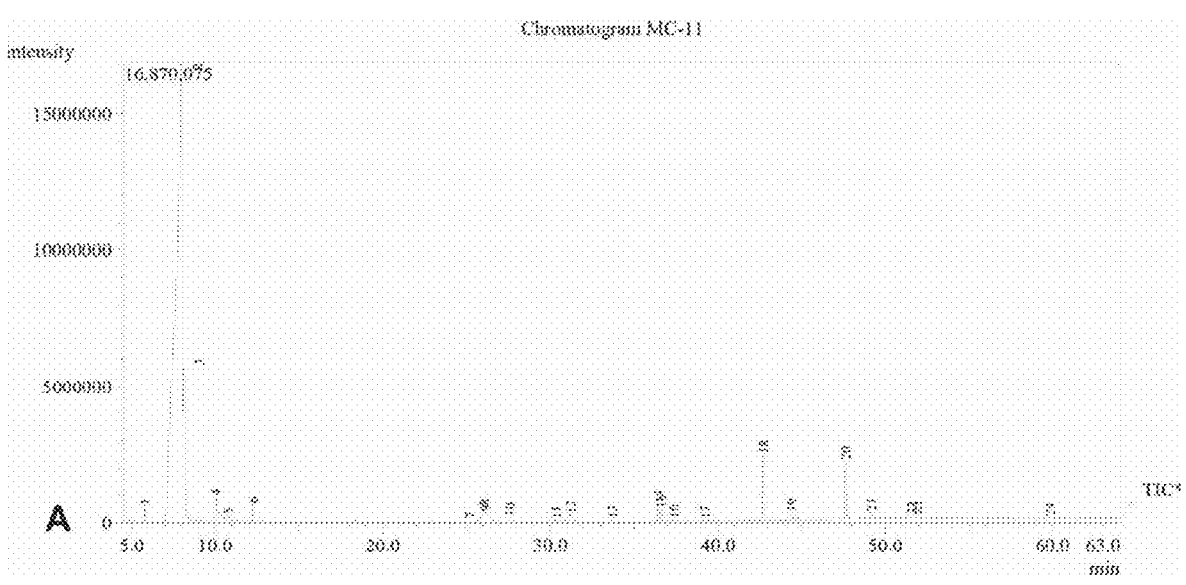
FIG. 4 depicts the GC MS analysis of extracted and purified PHB produced by *Iodobacter* sp. PCH 194: (a) gas chromatogram of methanolysed PHB (b) Mass spectra of PHB.
Figure 4:
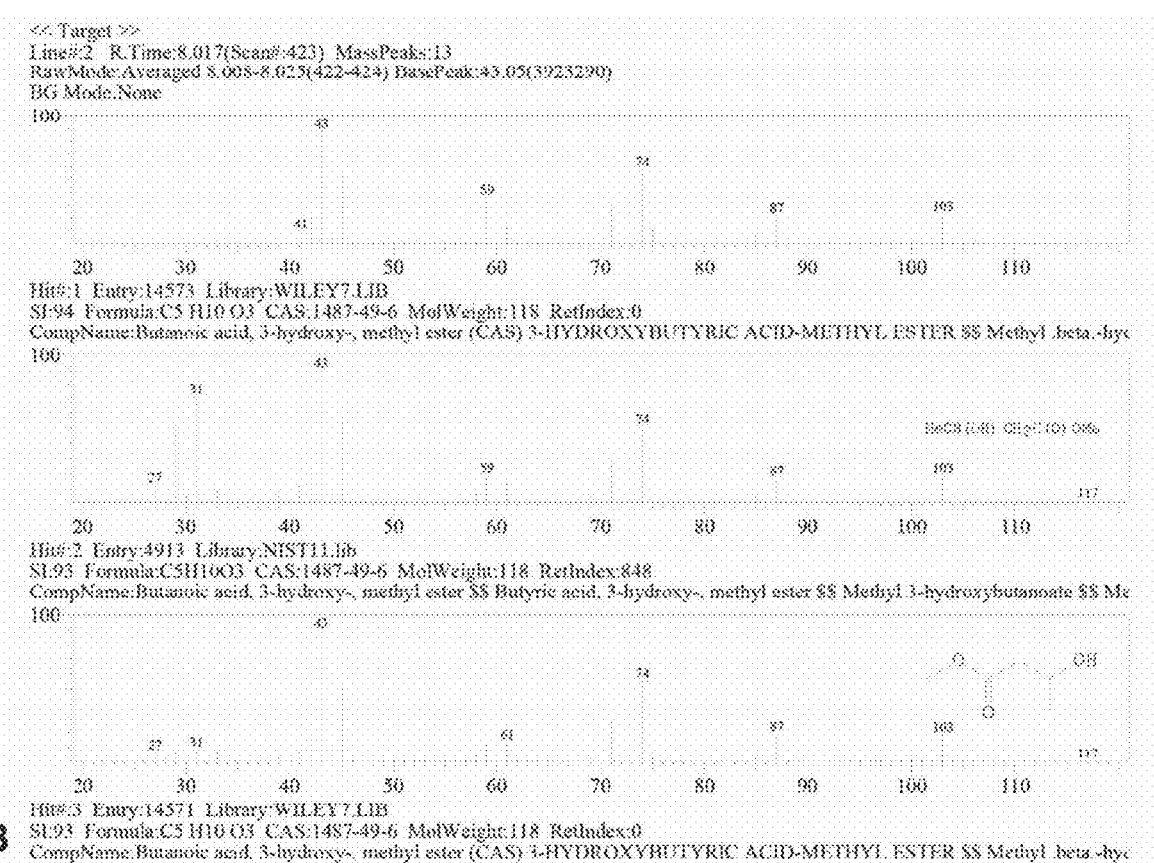
Figure 5:
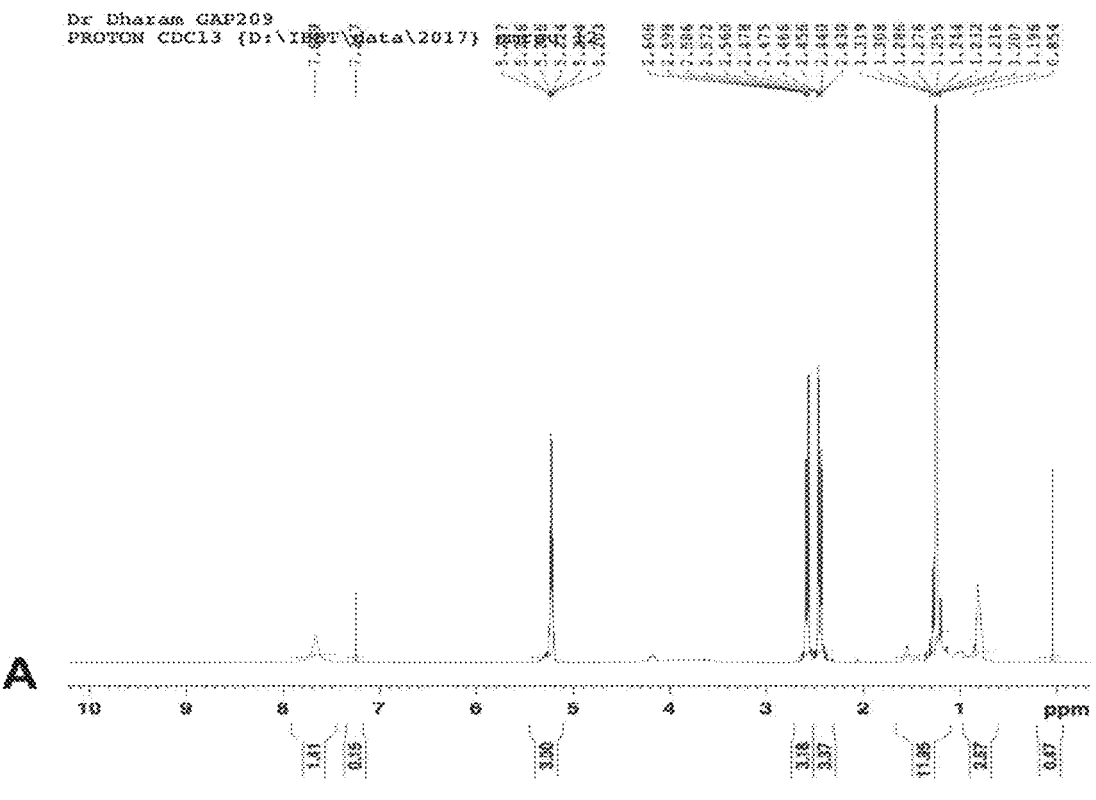
FIG. 5 depicts the NMR analysis of PHB produced by *Iodobacter* sp. PCH 194 (a) proton NMR (b) $^{13}$C NMR.
Figure 5:
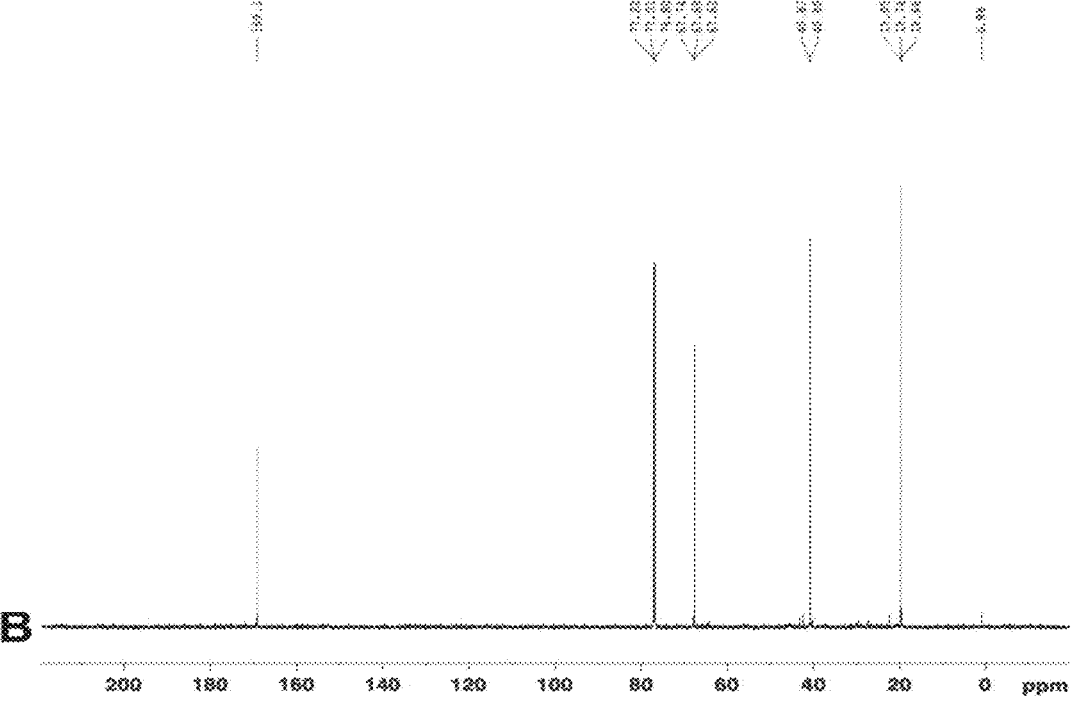

The extracted PHB was analyzed by GC-MS which revealed the 3-hydroxybutyrate as monomer (FIG. 4) and NMR (C and H) confirmed that the polymer is PHB (FIG. 5).

Furthermore, thermal properties analysis showed melting temperature (Tm) 178±5° C., and crystallization temperature (Tc) 50±5° C. (Table 1). These properties are comparable to the earlier reported PHB produced from other bacteria.

Figure 6:
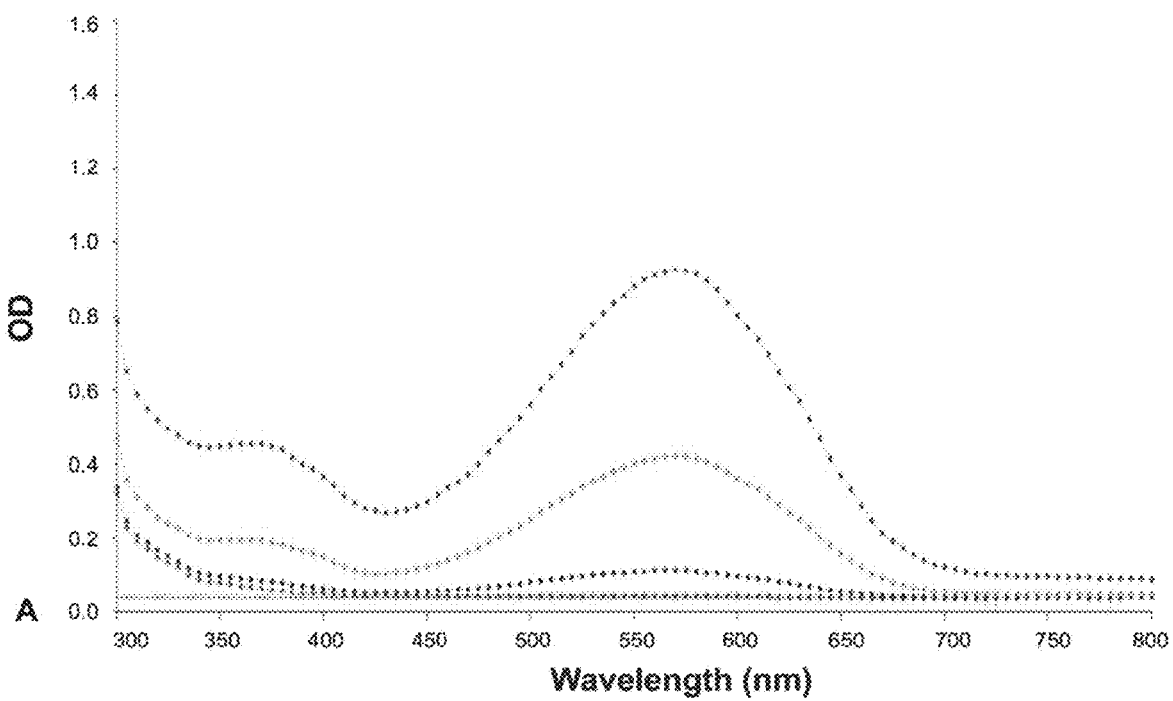
FIG. 6 depicts the violacein pigment monitoring using (a) spectrophotometer: visible spectra of crude violacein in red, green and blue, whereas pink color line represents the methanol control, (b) UPLC chromatogram of violacein pigment at 570 nm, and (c) Mass spectra of peaks: (c1) RT 5.1 matched with Violacein; molecular weight 343.342, MS mass 344.44 and (c2) RT 5.8 matched with deoxyviolacein; molecular weight 327.343, MS mass 328.41.
Figure 6:
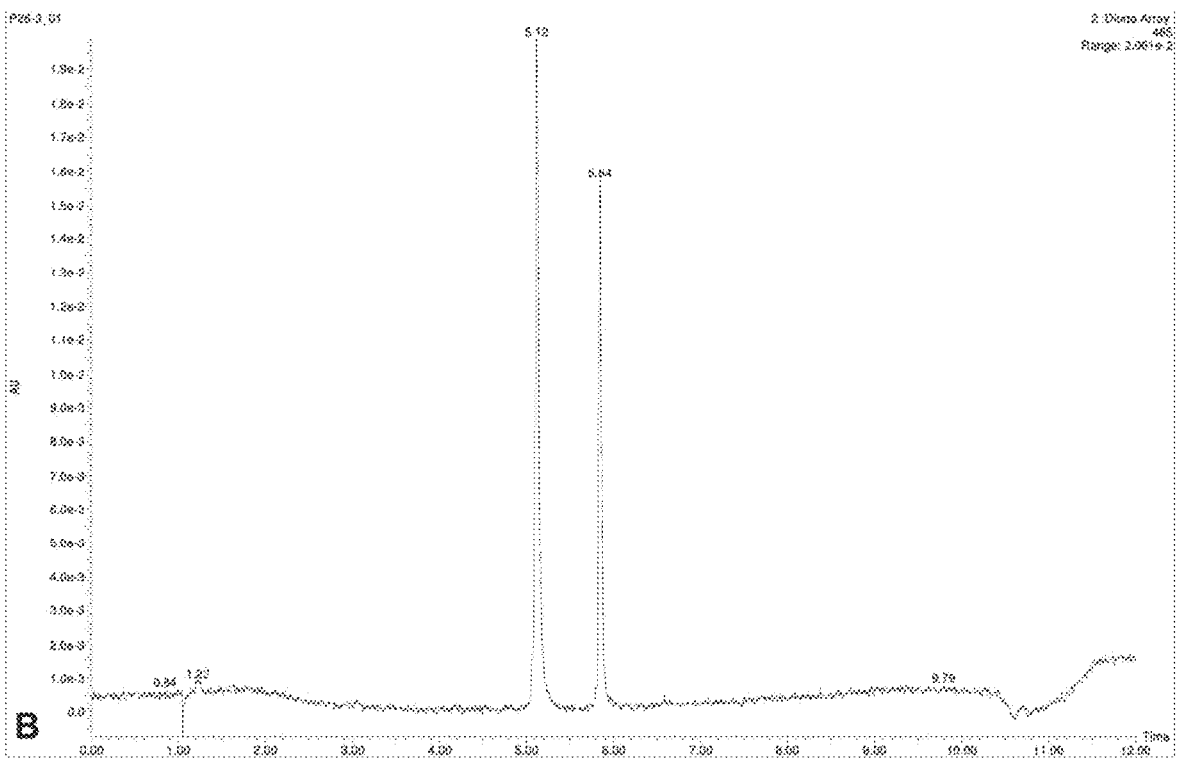
Figure 6:
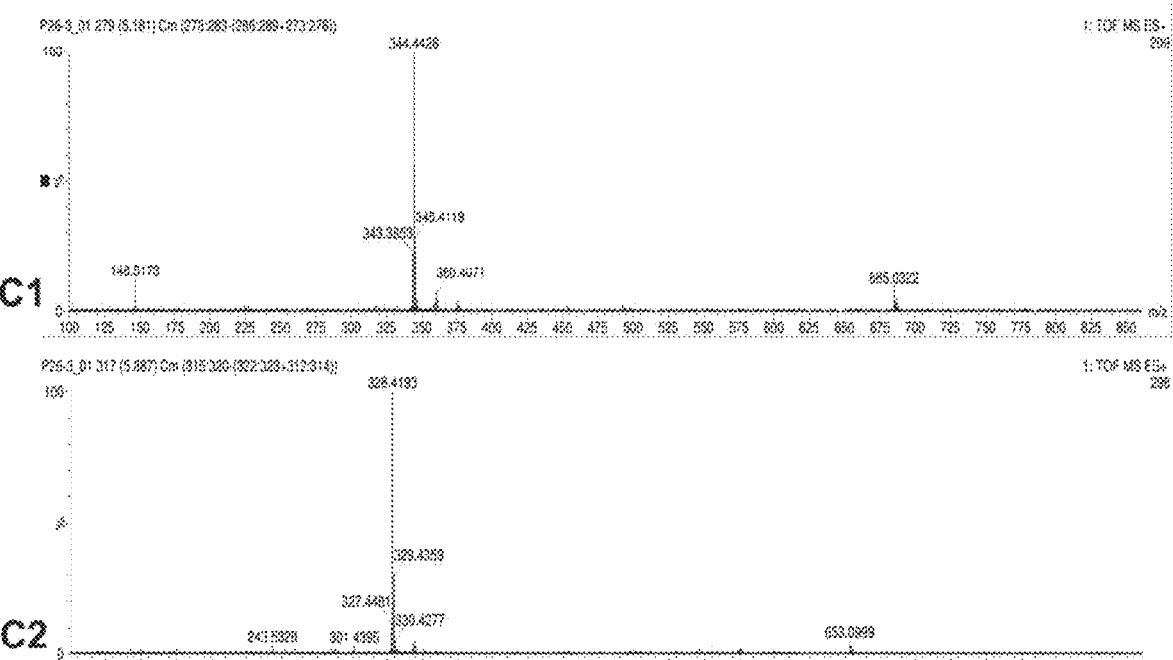

Methanol extracted crude violacein pigment analyzed using UPLC-MS showed >70% purity of the sample and presence of violacein >40% and deoxyviolacein in total mixture, and mass fragmentation pattern matched with the molecular weight of Violacein 343.342 g/mol and deoxyviolacein 327.343 g/mol, respectively (FIG. 6).

TABLE 1

| Analysis of thermal properties of PHB produced by *Iodobacter* sp. PCH194 | | |
| --- | --- | --- |
| Sample | Melting temperature (Tm) | Crystallization temperature (Tc) |
| PHB | 178 ± 5° C. | 50 ± 5° C. |

Example 1: Production of PHB in 7.5 Liter Working Volume of Fermenter with No $O_2$ Control Inoculating a loopful of *Iodobacter* sp. MTCC 25171 in 50 mL sterile nutrient broth medium and incubating at a temperature of 20±2° C. for 32 to 36 hours, at 100 to 200 rpm to obtain a seed culture for inoculating the production medium. Inoculating 4% (v/v) of seed (32 h old) to sterile 7.5 liter of production medium containing glucose 4% (w/v), tryptone 0.5% (w/v), NaCl 0.1% (w/v) and 25 mM $K_2HPO_4$/ $KH_2PO_4$ and pH 7.5. The fermentation was carried out for 96 hours at 100 rpm at 20° C. with no oxygen control. Biomass harvested after 96 hours to obtain cell pellet by centrifugation. The cell pellet was suspended in 3 times the volume of 1:1 trichloromethane and bleaching solution and incubated overnight at 37° C. with continuous shaking conditions. The mixture was kept for standing for a few minutes and the lower organic layer was pipetted out in a tube and further 3 to 5 times the volume of chilled methanol was added to it, mixed well and kept at –20° C. for a few minutes for precipitation. This reaction mixture was centrifuged to collect the precipitate and was dissolved in minimum amount of trichloromethane and precipitated with thrice the volume of methanol used. This reaction mixture was then centrifuged to collect the precipitated PHB and the residual solvent was removed by drying. The dried PHB was weighted and analyzed. The process resulted in 9 g/L dry cell weight biomass and 5 g/L of PHB.

Example 2: Production of PHB and Violacein Pigment in 7.5 Liter Working Volume of Fermenter Using 20% Dissolved $O_2$ Inoculating 4% (v/v) of the seed (36 h old) obtained in the manner as explained in example 1 to sterile 7.5 liter of production medium containing glucose 4.25% (w/v), tryptone 0.55% (w/v), NaCl 0.1% (w/v) and 25 mM $K_2HPO_4$/ $KH_2PO_4$ and pH 7.5. The fermentation was carried out for 96 hours at 150 rpm at 20° C. with 20% $pO_2$ automatic control. The biomass was harvested after 96 hours to obtain cell pellet by centrifugation. The process resulted in the production of colored biomass (around 19 g/L dry cell weight) after harvesting. Harvesting was done using micro-filtration of broth using Akta Flux system (GE Healthcare) with 0.2 μm hollow fiber cartridge. The violet pigmented cell slurry was collected and centrifuged. After centrifugation, both supernatant and pellets were collected for further extraction of Violacein pigment and polyhydroxybutyrate. Supernatant is highly viscous, therefore, treated with thrice the volume of methanol and stirred using magnetic stirrer. This mixture was again centrifuged and Violacein pigment collected as supernatant. The cell pellet was treated with 5 times the volume of methanol, mixed well at room tempera-ture and incubated for 10 min followed by centrifugation. This step was repeated twice and pellet became colorless. The collected Violacein pigment solution was concentrated in a rotary vacuum evaporator. Remaining cell pellet was mixed 5 times volume of 1:1 trichloromethane and bleach-ing solution and incubated overnight at 37° C. with con-tinuous shaking conditions. The mixture was kept for stand-ing for few minutes and lower organic layer pipetted. Added 5 times volume of chilled methanol to the pipetted organic solution; mixed well and kept in –20° C. for few minutes for precipitation. This reaction mixture centrifuged to collect precipitate, washed with twice the volume of methanol and residual solvent was removed by drying. The dried PHB was weighted and analyzed. The process resulted in around 19 g/L dry cell weight biomass, 10 g/L of PHB and 1.5-1.8 g/L of violacein pigment.

Example 3: Production of PHB and Violacein Pigment in 10 Liter Working Volume of Fermenter Using 20% Dissolved $O_2$ Inoculating 4% (v/v) of seed (36 h old) obtained in the manner as explained in example 1 to sterile 10 liter of production medium containing glucose 4.0% (w/v), tryptone 0.5% (w/v), NaCl 0.1% (w/v) and 25 mM $K_2HPO_4$/$KH_2PO_4$ and pH 7.5. The fermentation was carried out for 96 hours at 150 rpm at 20° C. with 20% $pO_2$ automatic control. Biomass was harvested after 96 hours to obtain cell pellet by centrifugation. Process results in the production of colored biomass after harvesting. Harvesting was done using micro-filtration of broth using Akta Flux system (GE Healthcare) with 0.2 μm hollow fiber cartridge. The violet pigmented cell pellet was collected and treated with 5 times of volume of methanol and stirred using magnetic stirrer. This mixture was again passed through Akta Flux microfiltration system. Violet colored filtrate is collected and concentrated in a rotary vacuum evaporator. Remaining colorless cell pellet was mixed in 3 times volume of 1:1 trichloromethane and bleaching solution and incubated overnight at 37° C. with continuous shaking conditions. The mixture was kept for standing for few minutes and lower organic layer pipetted. Added 5 times volume of chilled methanol to the pipetted organic solution; mixed well and kept in –20° C. for few minutes for precipitation. This reaction mixture centrifuged to collect precipitate, washed with 2 times volume of metha-nol and residual solvent removed by drying. Dried PHB was weighted and analyzed. The process results in 13 g/L dry cell weight biomass, 7 g/L of PHB and 0.8-1.2 g/L of violacein pigment.

Advantages of the Invention

The developed process yields two valuable products i.e. Polyhydroxybutyrate and Violacein pigment in a single fermentation followed by the downstream process to obtain the individual products.

Higher production of both products i.e. PHB and Viola-cein pigment in a single process.

Simple process for the separation, extraction, and recov-ery of Violacein pigment and PHB from the culture broth.

The process is performed without pH control.

Production medium is very simple.

The process yields 7 to 10 g/L of PHB (>50% of dry cell biomass) and 0.8 to 1.5 g/L violacein pigment from 7.5 or 10 liter working volume fermenter.

The bioprocess is economically attractive as the process yields two products in a single fermentation.

Violacein obtained from the process of the present dis-closure is established for its known important biological activities such as antioxidant, anti-tumoral, antibacterial, antiviral and antiprotozoal. The PHB based biopolymers obtained from the process of the present disclosure is useful for synthesizing biodegradable bioplastics.

The products of the present disclosure find immense application in chemical, cosmetics, biotechnology, bioplas-tics, and biomaterials sectors.

We claim:

1. A bioprocess for the simultaneous production of poly-hydroxybutyrate (PHB) and violet-blue violacein pigment using the isolated bacterial strain of *Iodobacter* sp. MTCC 25171, the process comprising the steps:

i) inoculating a loopful of *Iodobacter* sp. MTCC 25171 in 50 mL sterile nutrient broth medium and incubating at a temperature of 20±2° C. for 32 to 36 hours, at 100 to 200 rpm to obtain a seed culture for inoculating the production medium;

ii) inoculating 3 to 5% v/v of the seed culture as obtained in step [i] to a sterile production medium and incubat-ing for 36 to 100 hours at 100 to 200 rpm at a temperature of 20±2° C. to obtain a biomass;

iii) harvesting the biomass as obtained in step [ii] to obtain a pigmented cell pellet by centrifugation or microfil-tration;

iv) suspending the pigmented cell pellet as obtained in step [iii] in methanol or ethanol, in a volume ratio of 1:3 to 1:5 and mixing well for 10 to 15 minutes at room temperature followed by centrifugation to obtain a pigment in the supernatant; and repeating the step until no visible violet colour remains in the cell pellet to obtain a colourless cell pellet;

v) concentrating the supernatant as obtained in step [iv] using vacuum evaporation to obtain the desired viola-cein pigment;

vi) suspending the colourless cell pellet as obtained in step [iv] in 3 to 5 times the volume of 1:1 trichlo-romethane and bleaching solution, followed by incu-bating overnight at temperature ranging from 30 to 40° C. under continuous shaking to obtain a mixture;

vii) allowing the mixture as obtained in step [vi] to stand for 10 to 15 minutes and pipetting out the lower organic layer in a test-tube and then adding 3 to 5 times the volume of chilled methanol, followed by mixing it well and keeping at temperature ranging from minus 4 to minus 20° C. for 30 to 60 minutes for precipitation to obtain a reaction mixture;

viii) centrifuging the reaction mixture as obtained in step [vii] to collect the pellet as precipitate and removing the residual solvent;

ix) drying the pellet as obtained in step [viii] and re-dissolving it in trichloromethane; and x) repeating steps vi to viii and finally collecting the pellet of Polyhydroxybutyrate by allowing the residual solvent to evaporate.

2. The process as claimed in claim 1, wherein the 36 to 100 hour incubation of step ii) is performed at 20° C. and 150 rpm.

3. The process as claimed in claim 1, wherein the yield of PHB and violacein pigment in 1 liter culture after 96 hours of incubation is in range of 3 to 5 g/L, and 0.5 to 0.8 g/L, respectively.

4. The process as claimed in claim 1, wherein the 36 to 100 hour incubation of step ii) is carried out in a fermenter while maintaining 20% dissolved oxygen and 150 rpm.

5. The process as claimed in claim 1, wherein the yield of PHB and violacein pigment in 7.5 or 10 liter working volume of fermenter after 96 hours of incubation is in range of 7 to 10 g/L, and 0.8 to 1.5 g/L, respectively.

6. The process as claimed in claim 1, wherein the PHB obtained is useful for the preparation of biodegradable bio plastics.

* * * * *